(12) United States Patent
Tanaka et al.

(10) Patent No.: US 9,969,105 B2
(45) Date of Patent: May 15, 2018

(54) METHOD FOR PRODUCING AGROCHEMICAL GRANULES

(75) Inventors: Nobuyuki Tanaka, Takoaka (JP); Kazuhiro Shimanuki, Makinohara (JP)

(73) Assignee: Nippon Soda Co., Ltd., Tokyo (JP)

(*) Notice: Subject to any disclaimer, the term of this patent is extended or adjusted under 35 U.S.C. 154(b) by 592 days.

(21) Appl. No.: 14/001,268

(22) PCT Filed: Feb. 16, 2012

(86) PCT No.: PCT/JP2012/053631
§ 371 (c)(1),
(2), (4) Date: Aug. 23, 2013

(87) PCT Pub. No.: WO2012/117862
PCT Pub. Date: Sep. 7, 2012

(65) Prior Publication Data
US 2013/0328231 A1 Dec. 12, 2013

(30) Foreign Application Priority Data
Feb. 28, 2011 (JP) .................. 2011-042222

(51) Int. Cl.
B29C 47/00 (2006.01)
B29B 9/06 (2006.01)
A01N 25/12 (2006.01)

(52) U.S. Cl.
CPC ............... *B29B 9/06* (2013.01); *A01N 25/12* (2013.01)

(58) Field of Classification Search
CPC .................................. B29B 9/06; A01N 25/12
See application file for complete search history.

(56) References Cited

U.S. PATENT DOCUMENTS 4,877,840 A * 10/1989 Chu .................. B29B 9/00
264/117
2010/0289170 A1* 11/2010 Thepsimuang ........ C10G 73/40
264/142

FOREIGN PATENT DOCUMENTS

| EP | 0 721 734 A1 | 7/1996 | |
|---|---|---|---|
| EP | 0721734 A1 * | 7/1996 | ............. A01N 25/12 |
| JP | 08-092007 A | 4/1996 | |
| JP | 2003-171207 A | 6/2003 | |
| JP | 2003-252702 A | 9/2003 | |
| JP | 2004-043370 A | 2/2004 | |
| WO | WO 95/09532 A1 | 4/1995 | |

OTHER PUBLICATIONS

Firestone, David. (2013). Physical and Chemical Characteristics of Oils, Fats, and Waxes (3rd Edition). AOCS Press. Online version available at: http://app.knovel.com/hotlink/toc/id:kpPCCOFW02/physical-chemical-characteristics/physical-chemical-characteristics.*

Kutz, Myer. (2011). Applied Plastics Engineering Handbook—Processing and Materials. Elsevier. Online version available at: http://app.knovel.com/hotlink/toc/id:kpAPEHPMOD/applied-plastics-engineering/applied-plastics-engineering.*

Giles, Harold F. Jr. Wagner, John R. Jr. Mount, Eldridge, M. III. (2005). Extrusion—The Definitive Processing Guide and Handbook. (pp. 134-136). William Andrew Publishing/Plastics Design Library. Online version available at: http://app.knovel.com/hotlink/toc/id:kpETDPGH02/extrusion-definitive/extrusion-definitive.*

Supplementary European Search Report dated Aug. 12, 2014, in EP 12752099.7.

Database WPI Week 200406, Thomson Scientific, London, GB; AN 2004-055884 XP002728062, & JP 2003 171207 A (Mitsui Chem. Inc.) Jun. 17, 2003.

* cited by examiner

*Primary Examiner* — Galen H Hauth
(74) *Attorney, Agent, or Firm* — Foley & Lardner LLP

(57) ABSTRACT

The present invention provides a method for producing agrochemical granules, which contain an agrochemical active ingredient, one or more kinds of hydrophobic substances, and a substance capable of absorbing oil, with stable quality. The method for producing agrochemical granules of the present invention includes (i) a step of obtaining a mixture by mixing an agrochemical active ingredient, one or more kinds of hydrophobic substances, and a substance capable of absorbing oil together, (ii) a step of obtaining a kneaded material by loading the obtained mixture into a kneading device, kneading the mixture at a heating temperature equal to or higher than the highest melting point of the hydrophobic substances, and then causing the kneaded material to be discharged from the kneading device at a temperature equal to or lower than the highest melting point of the hydrophobic substances, and (iii) a step of granulating the obtained kneaded material by an extrusion molding method.

12 Claims, No Drawings

US 9,969,105 B2

METHOD FOR PRODUCING AGROCHEMICAL GRANULES

TECHNICAL FIELD

The present invention relates to a method for producing agrochemical granules. More specifically, the present invention relates to a method for producing agrochemical granules having stable quality and which contain an agrochemical active ingredient, one or more kinds of hydrophobic substances, and a substance capable of absorbing oil.

CROSS-REFERENCE TO RELATED APPLICATIONS

This application is a National Stage application of PCT/JP2012/053631, filed Feb. 16, 2012, which claims priority from Japanese Patent Application No. 2011-042222, filed Feb. 28, 2011, the content of which is incorporated herein by reference.

Priority is claimed on Japanese Patent Application No. 2011-042222, filed Feb. 28, 2011, the content of which is incorporated herein by reference.

BACKGROUND ART

As methods for producing agrochemical granules, the following methods are known. For example, PTL 1 discloses a production method in which a sustained-release agrochemical composition which contains an agrochemical active component, a hydrophobic substance having a boiling point of 50° C. or higher, a substance capable of absorbing oil, and a hydrophilic substance having a boiling point of 50° C. or higher are melted, and the resultant is granulated by extrusion under a condition of heating performed at a temperature equal to or higher than the melting point. Specifically, PTL 1 discloses a method in which 20 g of acetamiprid as an active substance, 620 g of precipitated calcium carbonate as a carrier, 20 g of polyvinyl alcohol as a release control agent, and 40 g of white carbon capable of absorbing oil are uniformly mixed together, 300 g of molten paraffin wax (melting point of about 70° C.) is added thereto, the mixture is kneaded with a kneader while being kept at a product temperature of 85° C., the kneaded material is granulated by being extruded through a screen, which is heated at 85° C. and has 1 mm openings, then ground with a disintegrator, and then the resultant is sieved and classified into granules of 0.8 mm to 2 mm in size.

PTL 2 discloses a method for producing agrochemical granules composed of an agrochemical active ingredient, a thermoplastic material, and an inorganic diluting carrier, through (i) a mixing step, (ii) a kneading step, and (iii) an extruding step. In this method, extruding granulation is performed at a temperature that is equal to or higher than a freezing point and lower than a melting point of the thermoplastic material. Specifically, PTL 2 discloses a method in which 2% by weight of dinotefuran as an agrochemical active ingredient, 20% by weight of montanoic acid ester wax as a thermoplastic material (melting point of 75° C. to 85° C. and a freezing point of 70° C. to 75° C.), 5% by weight of white carbon as an inorganic diluting carrier, 10% by weight of talc, and 63% by weight of calcium carbonate are loaded in to Henschel mixer and mixed together, the mixture is discharged as a powder at 76° C., the powder is loaded into a screw extrusion granulator (EXR-130) manufactured by Fuji Paudal Co., Ltd. and kneaded at 78° C., the resultant is granulated by being extruded through a die having 0.8 mm openings at 73° C. and then ground by a disintegrator, thereby obtaining granules.

PTL 3 discloses a method for producing an agrochemical composition composed of an agrochemical active ingredient, two or more kinds of hydrophobic substances, a substance capable of absorbing oil, and a carrier, through (i) a mixing step, (ii) a kneading step, and (iii) an extruding step. In this method for producing agrochemical granules, extruding granulation is performed at a temperature that is equal to or higher than a freezing point and lower than a melting point of a hydrophobic substance having a high melting point. Specifically, PTL 3 discloses a method in which 2% by weight of acetamiprid as an agrochemical active ingredient, 15% by weight of carnauba wax (melting point of 83° C. and a freezing point of 73° C. to 74° C.) and 5% by weight of paraffin wax (melting point of 70° C.) as hydrophobic substances, 5% by weight of white carbon as a substance capable of absorbing oil, 2% by weight of polyvinyl alcohol as a water-soluble substance, and 10% by weight of talc and 61% by weight of calcium carbonate as a carrier are loaded into a Henschel mixer and mixed together, the mixture is discharged as a granular material at 80° C., the granular material is loaded into a screw extrusion granulator (EXR-130) manufactured by Fuji Paudal Co., Ltd., kneaded at 80° C., and granulated at the same temperature by being extruded through a die having 0.8 mm openings, and the granules are further ground with a disintegrator, thereby obtaining agrochemical granules.

PRIOR ART LITERATURE

Patent Literature

[PTL 1] PCT International Publication No. WO95/09532
[PTL 2] Japanese Unexamined Patent Application, First Publication No. 2003-252702
[PTL 3] Japanese Unexamined Patent Application, First Publication No. 2004-43370

DISCLOSURE OF INVENTION

Problems to be Solved by the Invention

However, in view of stably producing granules having excellent quality, the above production methods are not satisfactory.

The present invention aims to provide a method for producing agrochemical granules containing an agrochemical active ingredient, one or more kinds of hydrophobic substances, and a substance capable of absorbing oil, with stable quality.

Means for Solving the Problems

The present inventors conducted thorough research regarding the reason why the quality is not stable in the above methods. As a result, they found that it is more important to regulate the temperature in the kneading step than to regulate the temperature in the extruding granulation step, and granules having excellent quality can be more stably produced if a temperature profile of the kneading step is controlled within a certain range. The present invention has been completed based on this knowledge.

That is, the present invention includes the following.

[1] A method for producing agrochemical granules, including (ii) a step of obtaining a kneaded material by loading an agrochemical active ingredient, one or more kinds of hydrophobic substances, and a substance capable of absorbing oil into a kneading device, kneading them at a heating temperature equal to or higher than the highest melting point of the hydrophobic substances, and then causing the material to be discharged from the kneading device at a temperature equal to or lower than the highest melting point of the hydrophobic substances, and (iii) a step of granulating the obtained kneaded material by an extrusion molding method.

[2] A method for producing agrochemical granules, including (i) a step of obtaining a mixture by mixing an agrochemical active ingredient, one or more kinds of hydrophobic substances, and a substance capable of absorbing oil together, (ii) a step of obtaining a kneaded material by loading the obtained mixture into a kneading device, kneading the mixture at a heating temperature equal to or higher than the highest melting point of the hydrophobic substances, and then causing the kneaded material to be discharged from the kneading device at a temperature equal to or lower than the highest melting point of the hydrophobic substances, and (iii) a step of granulating the obtained kneaded material by an extrusion molding method.

[3] The method for producing agrochemical granules according to [1] or [2], in which steps (ii) and (iii) are performed consecutively.

[4] The method for producing agrochemical granules according to any one of [1] to [3], further including a step of disintegrating the granulated material after step (iii).

[5] The method for producing agrochemical granules according to any one of [1] to [4], in which water solubility of the agrochemical active ingredient is 60 ppm or greater.

[6] The method for producing agrochemical granules according to any one of [1] to [5], in which the agrochemical active ingredient is at least one kind selected from the group consisting of nitenpyram, imidacloprid, acetamiprid, thiamethoxam, clothianidin, thiacloprid, and dinotefuran.

[7] The method for producing agrochemical granules according to any one of [1] to [6], in which the hydrophobic substance is at least one kind selected from the group consisting of carnauba wax, shellac, bees wax, Japan wax, rice wax, candelilla wax, fatty acids or hydrogenated products thereof that are obtained by decomposing vegetable fat-and-oil or animal fat-and-oil, stearic acid, behenic acid, hydrogenated fatty acids of rapeseed, hydrogenated palm fatty acids, hydrogenated fatty acids of beef tallow, hydrogenated castor oil, paraffin wax, microcrystalline wax, and montanoic acid ester wax.

[8] The method for producing agrochemical granules according to any one of [1] to [7], in which the substance capable of absorbing oil is at least one kind selected from the group consisting of amorphous silicon dioxide, starch, starch derivatives, and celluloses.

[9] The method for producing agrochemical granules according to any one of [1] to [8], further containing a release control agent.

[10] The method for producing agrochemical granules according to any one of [1] to [9], in which the content of the agrochemical active ingredient is 0.01 to 50% by weight, the content of the hydrophobic substance is 15 to 80% by weight, and the content of the substance capable of absorbing oil is 0.05 to 30% by weight.

[11] The method for producing agrochemical granules according to any one of [1] to [10], in which the kneading device is a continuous single-screw kneading device or a continuous double-screw kneading device.

EFFECTS OF THE INVENTION

According to the method for producing agrochemical granules of the present invention, it is possible to stably produce agrochemical granules containing an agrochemical active ingredient, one or more kinds of hydrophobic substances, and a substance capable of absorbing oil, with high quality.

BEST MODE FOR CARRYING OUT THE INVENTION

The method for producing agrochemical granules of the present invention includes (ii) a step of obtaining a kneaded material by loading an agrochemical active ingredient, one or more kinds of hydrophobic substances, and a substance capable of absorbing oil into a kneading device, kneading them at a heating temperature equal to or higher than the highest melting point of the hydrophobic substances, and then causing the kneaded material to be discharged from the kneading device at a temperature equal to or lower than the highest melting point of the hydrophobic substances, and (iii) a step of granulating the obtained kneaded material by an extrusion molding method.

In the present invention, the term "melting point that is the highest of the hydrophobic substances" refers to a melting point of a hydrophobic substance having the highest melting point among one or more kinds of the hydrophobic substances used in the method for producing agrochemical granules of the present invention.

The agrochemical active ingredient used in the present invention is not particularly limited as long as it can be formulated into granules by kneading and extruding granulation. In addition, the agrochemical active ingredient is preferably a substance having solubility in water of 60 ppm or greater. If an agrochemical active ingredient showing high solubility in water is used, the agrochemical active ingredient is rapidly released from the granules.

Specific examples of the agrochemical active ingredient include the following germicides, herbicides, insecticides and miticides, plant growth regulators, and the like.

<Germicides>

Captan, thiuram, ziram, zineb, maneb, mancozeb, propineb, polycarbamate, chlorothalonil, quintozene, captafol, iprodione, procymidone, fluoroimide, mepronil, flutolanil, pencycuron, oxycarboxin, fosetyl-aluminum, propamocarb, triadimefon, triadimenol, propiconazole, diclobutrazol, bitertanol, hexaconazole, myclobutanil, flusilazole, etaconazole, fluotrimazole, flutriafen, penconazole, diniconazole, cyproconazole, fenarimol, triflumizole, prochloraz, imazalil, pefurazoate, tridemorph, fenpropimorph, trifolin, buthiobate, pyrifenox, anilazine, polyoxin, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentin acetate, triphenyltin hydroxide, diethofencarb, quinomethionate, binapacryl, lecithin, sodium bicarbonate, dithianon, dinocap, fenaminosulf, diclomezine, guazatine, dodine, IBP, edifenphos, mepanipyrim, ferimzone, trichlamide, methasulfocarb, fluazinam, ethoquinolac, dimethomorph, phylloquinone, tecloftalam, phthalide, phenazine oxide, thiabendazole, tricyclazole, vinclozolin, cymoxanil, cyclobutanyl, guazatine, propamocarb hydrochloride, oxolinic acid, cyflufenamid, iminoctadine, kresoxim-methyl, triazine, fenhexamid, cyazofamid, cyprodinil, prothioconazole, fenbuconazole, trifloxystrobin, azoxystrobin, hexaconazole, imibenconazole, tebuconazole, difenoconazole, carpropamid, and the like.

<Herbicides>

2,4-D, MCPA, clomeprop, dicamba, chlorotoluron, diuron, linuron, isouron, fenuron, neburon, simazine, atrazine, simetryn, prometryn, hexazinone, propazine, desmetryne, terbumeton, propanil, bromoxynil, ioxynil, pyridate, chloridazon, bentazon, chlomethoxyfen, bifenox, sodium acifluorfen, flumioxazin, thiadiazine, oxadiazon, sulfentrazone, pentoxazone, pyraclonil, pyrazolynate, pyrazoxyfen, benzofenap, mesotrione, isoxaflutole, isoxachlortole, amitrole, aclonifen, diflufenican, benzobicyclon, diclofop-methyl, fluazifop-butyl, alloxydim sodium, clethodim, sethoxydim, tralkoxydim, tepraloxydim, bensulfuron-methyl, pyrazosulfuron-ethyl, rimsulfuron, imazosulfuron, prosulfuron, fulmetsulam, diclosulam, metosulfam, imazapyr, imazaquin, pyrithiobac-sodium, bispyribac-sodium, pyriminobac-methyl, flucarbazone, propoxycarbazone, glyphosate, a glyphosate ammonium salt, gluphosinate, trifluralin, pendimethalin, benfluralin, prodiamine, propham, dithiopyr, alachlor, metolachlor, pethoxamid, acetochlor, propachlor, dimethenamid, diphenamid, napropamide, mefenacet, fentrazamide, molinate, dimepiperate, cycloate, esprocarb, thiobencarb, thiocarbazil, bensulide, dalapon, asulam, DNOC, dinoseb, flupoxam, triaziflam, quinclorac, cinmethylin, dazomet, dymron, etobenzanide, oxaziclomefone, pyributicarb, and the like.

<Insecticides and Miticides>

Insecticides based on organic organophosphorus or carbamate: fenthion, fenitrothion, diazinon, chlorpyrifos, ESP, vamidothion, phenthoate, dimethoate, formothion, malathon, trichlorfon, thiometon, phosmet, dichlorvos, acephate, EPBP, methyl parathion, oxydemeton-methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenophos, pyraclofos, monocrotophos, azinphos-methyl, aldicarb, mesomil, thiodicarb, carbofuran, carbosulfan, benfuracarb, furathiocarb, propoxur, BPMC, MTMC, MIPC, carbaryl, pirimicarb, ethiofencarb, fenoxycarb, cartap, thiocyclam, bensultap, and the like.

Pyrethroid-based insecticides: permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, ethofenprox, cycloprothrin, tralomethrin, silafluofen, acrinatrhin, and the like.

Benzoylurea-based insecticides and others: diflubenzuron, chlorfluazuron, hexaflumuron, triflumuron, flufenoxuron, flucycloxuron, buprofezin, pyriproxyfen, methoprene, benzoepin, diafenthiuron, imidacloprid, fipronil, nicotine sulfate, rotenone, metaldehyde, acetamiprid, chlorfenapyr, nitenpyram, thiacloprid, clothianidin, thiamethoxam, dinotefuran, indoxacarb, pymetrozine, spinosad, emamectin, pyridalyl, tebufenozide, chromafenozide, methoxyfenozide, tolfenpyrad, and the like.

Nematocides: fenamiphos, fosthiazate, cadusafos, and the like.

Miticides: Chlorobenzilate, phenisobromolate, dicofol, amitraz, BPPS, benzomate, hexathiazox, fenbutatin oxide, polynactin, quinomethionate, CPCBS, tetradifon, avermectin, milbemectin, clofentezine, cyhexatin, pyridaben, fenpyroximate, tebufenpyrad, pyrimidifen, fenothiocarb, dienochlor, fluacrypyrim, acequinocyl, bifenazate, ethoxazol, spirodiclofen, fenazaquin, and the like.

<Plant Growth Regulators>

Gibberellins (for example, gibberellin A3, gibberellin A4, and gibberellin A7), IAA, NAA, and the like.

Among these, the agrochemical active ingredient is preferably at least one kind selected from the group consisting of nitenpyram, imidacloprid, acetamiprid, thiamethoxam, clothianidin, thiacloprid, and dinotefuran.

The content of the agrochemical active ingredient in the agrochemical granules is preferably 0.01 to 50% by weight and more preferably 0.01 to 20% by weight.

The hydrophobic substance used in the present invention is not particularly limited as long as it can be formulated into granules by kneading and extruding granulation. The melting point of the hydrophobic substance is preferably 50° C. to 120° C. and more preferably 50° C. to 100° C. Examples of the hydrophobic substance include carnauba wax, shellac, bees was, Japan wax, rice wax, candelilla wax, fatty acids or hydrogenated products thereof that are obtained by decomposing vegetable fat-and-oil or animal fat-and-oil, stearic acid, behenic acid, hydrogenated fatty acids of rapeseed, hydrogenated palm fatty acids, hydrogenated fatty acids of beef tallow, hydrogenated castor oil, paraffin wax, microcrystalline wax, and montanoic acid ester wax, and the like. These can be used alone, or two or more kinds of these can be used in combination.

The content of the hydrophobic substance in the agrochemical granules is preferably 15 to 80% by weight and more preferably 18 to 70% by weight. Moreover, if a hydrophobic substance showing a high degree of crystallinity is used, the agrochemical active ingredient is slowly released from the granules.

The substance capable of absorbing oil that is used in the present invention is a substance that can absorb a molten hydrophobic substance and can be turned into powder outwardly. Specific examples thereof include starch, starch derivatives, celluloses, amorphous silicon dioxide, and the like. One kind of these can be used alone, or two or more kinds of these may be used in combination.

The amorphous silicon dioxide can be produced by a wet method and is called white carbon in general. Examples of commercially available products of the amorphous silicon dioxide include Carplex #67, Carplex #80, Carplex CS-5, Carplex CS-7, (all manufactured by Shionogi & Co., Ltd.) and the like.

Among the agrochemical granules, the content of the substance capable of absorbing oil is preferably 0.05 to 30% by weight and more preferably 0.5 to 20% by weight.

In the present invention, in addition to the agrochemical active ingredient, hydrophobic substance, and substance capable of absorbing oil, additives that can be contained in agrochemical granules may be used. Examples of the additives include a release control agent, a binder, a bulking agent, a surfactant, a carrier, a colorant, and the like.

Examples of the release control agent include water-soluble polymers, water-soluble inorganic substances, water-soluble organic substances, and the like. Examples of the water-soluble polymers include alginic acid, sodium alginate, xanthan gum, carrageenan, karaya gum, hydroxypropyl cellulose, hydroxypropyl methylcellulose, hydroxypropyl starch; polyvinyl alcohol, carboxyvinyl polymers, sodium polyacrylate, and the like. Examples of the water-soluble inorganic or organic substances include sodium sulfate, sodium chloride, citric acid or a salt thereof, adipic acid or a salt thereof, urea, pregelatinized starch, lactose, and the like. The content of the release control agent in the agrochemical granules is preferably 0 to 50% by weight and more preferably 0.01 to 40% by weight.

Examples of the carrier or bulking agent include clay, talc, calcium carbonate, and the like. The carrier or bulking agent is used in an amount such that the total amount of the agrochemical active ingredient, hydrophobic substance, substance capable of absorbing oil, and release control agent plus the carrier or bulking agent becomes 100% by weight.

(i) Mixing Step

First, in the method for producing agrochemical granules of the present invention, the agrochemical active ingredient, one or more kinds of hydrophobic substances, the substance capable of absorbing oil, and other optional additives can be mixed with together. The order of mixing the respective components, the mixing method, and the like are not particularly limited. The obtained mixture is preferably in a powder or granule state, since the mixture is easy to handle and transferred easily to the next step in this state. In addition, the mixing may be performed in the kneading step described below.

(ii) Kneading Step

In the kneading step, first, the agrochemical active ingredient, one or more kinds of hydrophobic substances, the substance capable of absorbing oil, and other optional additives are loaded in a kneading device. The order of loading the respective components into the kneading device is not particularly limited. The agrochemical active ingredient, one or more kinds of hydrophobic substances, the substance capable of absorbing oil, and other additives which are optionally added may be loaded into the kneading device after being made into a mixture by the above mixing step.

The temperature of the agrochemical active ingredient, one or more kinds of hydrophobic substances, the substance capable of absorbing oil, and other optional additives that are loaded into the kneading device, or the temperature of the mixture of these is not particularly limited, but is preferably 0° C. to 50° C. and more preferably 5° C. to 45° C.

Next, the agrochemical active ingredient, one or more kinds of hydrophobic substances, the substance capable of absorbing oil, and other optional additives are heated and kneaded in the kneading device. In the present invention, the heating temperature in the kneading device needs to reach a temperature equal to or higher than the highest melting point of the hydrophobic substances, at least once. The lower limit of the highest heating temperature is preferably 4° C. higher than the highest melting point of the hydrophobic substances loaded into the kneading device, more preferably 8° C. higher than the melting point, and even more preferably 10° C. higher than the melting point. The upper limit of the heating temperature is not particularly limited, as long as the agrochemical active ingredient, one or more kinds of hydrophobic substances, the substance capable of absorbing oil, and other optional additives are not thermally decomposed. However, the upper limit is generally 130° C., preferably 120° C., and more preferably 115° C.

Heating can be performed by, for example, causing a medium such as steam or hot water to flow in a jacket mounted on the kneading device, or by applying electricity to an electric heater mounted on the kneading device. In view of ease of regulating temperature, a high thermal conduction efficiency, and the like, heating by a jacket is preferable.

The kneading device is not particularly limited as long as it can perform kneading by applying heat, and examples thereof include single-screw kneading devices, double-screw kneading devices, roll kneaders, and the like. Among these, a continuous single-screw kneading device or a continuous double-screw kneading device is preferable, and a double-screw kneading device is more preferable in the respect that a temperature profile is easily controlled, and the kneading state is easily regulated. In a continuous kneading device, the portion from the opening for injecting raw material components to the opening for discharging the kneaded material can be divided into plural sections. Moreover, the respective sections can be controlled to have different temperatures and to be in different kneading states.

The kneading state can be designed by the combination of a paddle and a screw installed in the kneading device. Examples of the paddle include a paddle for kneading (flat paddle), a paddle having a function of feeding in addition to a function of kneading (helical paddle), a paddle having a function of backward feeding in addition to a function of kneading (backward helical paddle), and the like. When the paddle rotates, the kneaded material undergoes volumetric change by compression or stretching and is influenced by a shearing action between a trough and a paddle or between paddles.

Finally, the kneading material is discharged from the kneading device. The upper limit of the temperature (product temperature) at the time of discharging is preferably the same temperature as the highest melting point of the hydrophobic substances, preferably a temperature 2° C. lower than the melting point, and more preferably a temperature 4° C. lower than the melting point. The lower limit of the temperature (product temperature) at the time of discharging is not particularly limited as long as it is a temperature at which the kneaded material does not coagulate. However, the lower limit is generally 60° C., preferably 65° C., and more preferably 70° C.

By the heat applied from the outside or the heat caused by friction or the like, the product temperature of the kneaded material in the kneading device can slowly increase immediately after the material is loaded into the kneading device and reach a temperature equal to or higher than the highest melting point of the hydrophobic substances. In order to control the temperature (product temperature) at the time of discharging to fall within the above temperature range, in the section close to the opening for discharging kneaded material of the kneading device, it is preferable to regulate the product temperature of the kneaded material by causing hot water at low temperature or the like to flow in the jacket. The heating temperature in the section close to the opening for discharging kneaded material of the kneading device is preferably 30° C. to 70° C. and more preferably 35° C. to 60° C.

Moreover, if a kneading device equipped with a vent is used, unnecessary volatile components can be removed by evaporation in the kneading step.

(ii) Extruding Granulation Step

Subsequently, the obtained kneaded material is granulated by an extrusion molding method. If the extrusion molding device has a kneading function, this is preferable since the above kneading step and the extruding granulation step can be performed consecutively. The conditions of extrusion molding are not particularly limited. The upper limit of the temperature at the time of extruding the kneaded material is preferably the same temperature as the melting point that is the highest of the hydrophobic substances, more preferably a temperature 2° C. lower than the melting point, and even more preferably a temperature 4° C. lower than the melting point. The lower limit of the temperature at the time of extrusion is not particularly limited as long as it is a temperature at which the kneaded material does not coagulate. However, the lower limit is generally 60° C., preferably 62° C., and more preferably 65° C. If the temperature at the time of extrusion is too high, sometimes the obtained granulated materials adhere to or are fused with each other and are shaped into Ame (a type of Japanese candy) or Dango (a type of Japanese dumpling). If the temperature at the time of extrusion is too low, sometimes the granulated materials have irregular shapes, or the amount of a powdery material increases. The extruded kneaded material having a string-like shape is cut with a cutter to a predetermined size. It is preferable that the granulated material obtained by the extruding and molding granulation step have an approximately cylindrical shape. The size of the granulated material can be appropriately adjusted according to the specification of the agrochemical granules.

(iv) Disintegrating Step

The obtained granulated material is cooled. Sometimes the cooled granulated material contains materials fused with or adhering to each other. In this case, a disintegrating step can be performed. The granulated material can be disintegrated using a known disintegrating device. Moreover, the granulated material can optionally be dried or classified. In the manner described above, agrochemical granules can be obtained.

EXAMPLES

Hereinafter, the present invention will be described in more detail based on examples, but the present invention is not limited to these examples.

Example 1

20 parts by weight of acetamiprid (Mospiran raw material [purity of 99.0% or higher], manufactured by NIPPON SODA CO., LTD.) as an agrochemical active ingredient, 605 parts by weight of sedimentary calcium carbonate, 100 parts by weight of talc (supplier: Neolight Co., Ltd.), 50 parts by weight of silicon dioxide (Carplex #80, manufactured by Shionogi & Co., Ltd.), 15 parts by weight of polyvinyl alcohol (Gohsenol GL-05S, manufactured by The Nippon Synthetic Chemical Industry Co., Ltd.), 57 parts by weight of ground paraffin wax (WAX150, melting point of 65.5° C. to 68.2° C., manufactured by NIPPON SEIRO CO., LTD.), and 153 parts by weight of ground carnauba wax (melting point of 84±3° C.) were loaded into a ribbon mixer and mixed together.

The obtained mixture (a product temperature of about 23° C.) was loaded into a continuous double-screw kneading device (KRC kneader, manufactured by KURIMOTO, LTD.) so as to be kneaded under heating, and discharged from the continuous double-screw kneading device at a product temperature of 75° C. The continuous double-screw kneading device was divided into two sections. The heating temperature of the section (first section) close to the opening for injecting mixture was set to 89° C. by causing steam to flow in the jacket. The heating temperature of the section (second section) close to the opening for discharging kneaded material was set to 43° C. by causing hot water to flow in the jacket.

The obtained kneaded material (a product temperature of 75° C.) was loaded into an extrusion granulator (Fine Riu User EXRC JS-100, manufactured by Dalton Co., Ltd.) and granulated by extrusion at an extrusion temperature of 73° C., and as a result, a granulated material having a uniform cylindrical shape was obtained. In the granulated material, granules fused with or adhering to each other practically were not observed.

The granulated material was dried in a fluidized bed and then cooled to room temperature. Thereafter, the granulated material was disintegrated with a disintegrator and classified to a size of 1000 μm to 1400 μm by using a sieve, thereby obtaining granules. The yield of granules from the kneaded material was 84%.

Example 2

20 parts by weight of acetamiprid (Mospiran raw material [purity of 99.0% or higher], manufactured by NIPPON SODA CO., LTD.) as an agrochemical active ingredient, 605 parts by weight of sedimentary calcium carbonate, 100 parts by weight of talc (supplier: Neolight Co., Ltd.), 50 parts by weight of silicon dioxide (Carplex #80, manufactured by Shionogi & Co., Ltd.), 15 parts by weight of polyvinyl alcohol (Gohsenol GL-05S, manufactured by The Nippon Synthetic Chemical Industry Co., Ltd.), 57 parts by weight of ground paraffin wax (WAX-150, melting point of 65.5° C. to 68.2° C., manufactured by NIPPON SEIRO CO., LTD.), and 153 parts by weight of ground carnauba wax (melting point of 83±3° C.) were loaded into a ribbon mixer and mixed together.

The obtained mixture (a product temperature of about 33° C.) was loaded into a continuous double-screw kneading device (KRC kneader, manufactured by KURIMOTO, LTD.) so as to be kneaded under heating, and discharged from the continuous double-screw kneading device at a product temperature of 70° C. The continuous double-screw kneading device was divided into two sections. The heating temperature of the section (first section) close to the opening for injecting mixture was set to 110° C. by causing steam to flow in the jacket. The heating temperature of the section (second section) close to the opening for discharging kneaded material was set to 42° C. by causing hot water to flow in the jacket.

The obtained kneaded material (a product temperature of 70° C.) was loaded into an extrusion granulator (Fine Riu User EXRC JS-100, manufactured by Dalton Co., Ltd.) and granulated by extrusion at a granulation temperature of 72° C., and as a result, a granulated material having a uniform cylindrical shape was obtained. In the granulated material, granules fused with or adhering to each other were practically not observed.

The granulated material was cooled to room temperature in a dryer (vibro-fluidized bed dryer, manufactured by TOKUJU CORPORATION). Thereafter, the granulated material was disintegrated with a disintegrator and classified to a size of 2000 μm to 710 μm by using a sieve (a round vibration sifter, manufactured by TOKUJU CORPORATION), thereby obtaining granules. The yield of granules from the kneaded material was 91%.

Comparative Example 1

Granules were produced in the same manner as in Examples 1, except that in the continuous double-screw kneading device, the heating temperature of the section (first section) close to the opening for injecting kneaded material was changed to 113° C., the heating temperature of the section (second section) close to the opening for discharging kneaded material was changed to 103° C., and the product temperature at the time when the kneaded material was discharged from the continuous double-screw kneading device was changed to 84° C. As a result, a slightly soft kneaded material was obtained. The granulated material contained a large amount of granules that adhered to or were fused with each other. The yield of granules from the kneaded material was 81%.

Comparative Example 2

Granules were obtained in the same manner as in Example 1, except that in the continuous double-screw kneading device, the heating temperature of the section (first section) close to the opening for injecting kneaded material was changed to 90° C., the heating temperature of the section (second section) close to the opening for discharging kneaded material was changed to 22° C., and the product temperature at the time when the kneaded material was discharged from the continuous double-screw kneading device was changed to 76° C. As a result, due to insufficient kneading, a kneaded material having hard surfaces was obtained. The granulated material contained an extremely large amount of powdery materials or finely split materials. The yield of granules from the kneaded material was 72%.

Comparative Example 3

An attempt at producing granules was made in the same manner as in Example 1, except that in the continuous double-screw kneading device, the heating temperature of the section (first section) close to the opening for injecting kneaded material was changed to 85° C., the heating temperature of the section (second section) close to the opening for discharging kneaded material was changed to 55° C., and the product temperature at the time when the kneaded material was discharged from the continuous double-screw kneading device was changed to 79° C. As a result, due to insufficient kneading, a powdery kneaded material was obtained, and extruding granulation could not be performed.

Comparative Example 4

An attempt at producing granules was made in the same manner as in Example 1, except that in the continuous double-screw kneading device, the heating temperature of the section (first section) close to the opening for injecting kneaded material was changed to 95° C., the heating temperature of the section (second section) close to the opening for discharging kneaded material was changed to 95° C., and the product temperature at the time when the kneaded material was discharged from the continuous double-screw kneading device was changed to 98° C. As a result, an extremely soft kneaded material was obtained. The materials extruded from the granulating machine adhered to or were fused with each other, and formed a shape of candies or dumplings. Accordingly, they could not be granulated.

INDUSTRIAL APPLICABILITY

According to the method for producing agrochemical granules of the present invention, it is possible to stably produce agrochemical granules containing an agrochemical active ingredient, one or more kinds of hydrophobic substances, and a substance capable of absorbing oil, with high quality. Accordingly, the present invention is extremely useful in the industrial field.

The invention claimed is:

1. A method for producing agrochemical granules, comprising:
    (i) obtaining a kneaded material by loading a mixture of the agrochemical granules, comprising an agrochemical active ingredient, one or more kinds of hydrophobic substances, and a substance capable of absorbing oil into a kneading device, and kneading the mixture, and then causing the kneaded material to be discharged from the kneading device at a temperature which is at least 4° C. lower than the highest melting point of the hydrophobic substances and is 60° C. or higher; and
    (ii) granulating the obtained kneaded material by an extrusion molding method, wherein
        the agrochemical active ingredient is at least one kind selected from the group consisting of nitenpyram, imidacloprid, acetamiprid, thiamethoxam, clothianidin, thiacloprid, and dinotefuran,
        the hydrophobic substance is at least one kind selected from the group consisting of carnauba wax, shellac, bees wax, Japan wax, rice wax, candelilla wax, fatty acids or hydrogenated products thereof that are obtained by decomposing vegetable fat-and-oil or animal fat-and-oil, stearic acid, behenic acid, hydrogenated fatty acids of rapeseed, hydrogenated palm fatty acids, hydrogenated fatty acids of beef tallow, hydrogenated castor oil, paraffin wax, microcrystalline wax, and montanoic acid ester wax,
        the substance capable of absorbing oil is at least one kind selected from the group consisting of amorphous silicon dioxide, starch, starch derivatives, and celluloses,
        the content of the agrochemical active ingredient is 0.01 to 50% by weight, the content of the hydrophobic substance is 15 to 80% by weight, and the content of the substance capable of absorbing oil is 0.05 to 30% by weight,
        the kneading device is a continuous single-screw kneading device or a continuous double-screw kneading device, the kneading device is divided into two sections; a first section close to an opening for loading the mixture and a second section close to an opening for discharging the kneaded material, and
        while kneading, the heating temperature of the section close to the opening for loading the mixture is at least 2° C. higher than the highest melting point of the hydrophobic substances and is 130° C. or lower, and the heating temperature of the section close to the opening for discharging the kneaded material is 30° C. to 70° C.

2. A method for producing agrochemical granules, comprising:
    (i) obtaining a mixture by mixing an agrochemical active ingredient, one or more kinds of hydrophobic substances, and a substance capable of absorbing oil together;
    (ii) obtaining a kneaded material by loading the obtained mixture into a kneading device, kneading the mixture, and then causing the kneaded material to be discharged from the kneading device at a temperature which is at least 4° C. lower than the highest melting point of the hydrophobic substances and is 60° C. or higher; and
    (iii) granulating the obtained kneaded material by an extrusion molding method, wherein
        the agrochemical active ingredient is at least one kind selected from the group consisting of nitenpyram, imidacloprid, acetamiprid, thiamethoxam, clothianidin, thiacloprid, and dinotefuran,
        the hydrophobic substance is at least one kind selected from the group consisting of carnauba wax, shellac, bees wax, Japan wax, rice wax, candelilla wax, fatty acids or hydrogenated products thereof that are obtained by decomposing vegetable fat-and-oil or animal fat-and-oil, stearic acid, behenic acid, hydrogenated fatty acids of rapeseed, hydrogenated palm fatty acids, hydrogenated fatty acids of beef tallow, hydrogenated castor oil, paraffin wax, microcrystalline wax, and montanoic acid ester wax,
the substance capable of absorbing oil is at least one kind selected from the group consisting of amorphous silicon dioxide, starch, starch derivatives, and celluloses,
the content of the agrochemical active ingredient is 0.01 to 50% by weight, the content of the hydrophobic substance is 15 to 80% by weight, and the content of the substance capable of absorbing oil is 0.05 to 30% by weight,
the kneading device is a continuous single-screw kneading device or a continuous double-screw kneading device, the kneading device is divided into two sections; a first section close to an opening for loading the mixture and a second section close to an opening for discharging the kneaded material, and
while kneading, the heating temperature of the section close to the opening for loading the mixture is at least 2° C. higher than the highest melting point of the hydrophobic substances and is 130° C. or lower, and the heating temperature of the section close to the opening for discharging the kneaded material is 30° C. to 70° C.

3. The method for producing agrochemical granules according to claim 1, wherein steps (i) and (ii) are performed consecutively.

4. The method for producing agrochemical granules according to claim 1, further comprising: disintegrating the granulated material after step (ii).

5. The method for producing agrochemical granules according to claim 1, wherein water solubility of the agrochemical active ingredient is 60 ppm or greater.

6. The method for producing agrochemical granules according to claim 1, wherein the components of the agrochemical granules loaded in step (i) further comprise a release control agent.

7. The method for producing agrochemical granules according to claim 2, wherein steps (ii) and (iii) are performed consecutively.

8. The method for producing agrochemical granules according to claim 2, further comprising: disintegrating the granulated material after step (iii).

9. The method for producing agrochemical granules according to claim 2, wherein water solubility of the agrochemical active ingredient is 60 ppm or greater.

10. The method for producing agrochemical granules according to claim 2, wherein the mixture in step (i) further comprises a release control agent.

11. The method for producing agrochemical granules according to claim 1, wherein the kneading device is heated by a jacket mounted thereon.

12. The method for producing agrochemical granules according to claim 1, wherein the kneading device is equipped with a vent to remove unnecessary volatile components in the kneading step.

* * * * *